United States Patent [19]

Eckhardt

[11] Patent Number: 4,762,826

[45] Date of Patent: Aug. 9, 1988

[54] MICROBICIDES

[75] Inventor: Wolfgang Eckhardt, Lörrach, Fed. Rep. of Germany

[73] Assignee: Ciba-Geigy Corporation, Ardsley, N.Y.

[21] Appl. No.: 34,196

[22] Filed: Apr. 6, 1987

[30] Foreign Application Priority Data

Apr. 11, 1986 [CH] Switzerland .................. 1433/86
Feb. 27, 1987 [CH] Switzerland .................. 754/87

[51] Int. Cl.$^4$ .................. A01N 55/00; C07E 7/10
[52] U.S. Cl. .................. 514/63; 544/58.2; 544/59; 544/69; 546/14; 548/406
[58] Field of Search .................. 514/63; 544/58.2, 59, 544/69; 546/14; 548/406

[56] References Cited

FOREIGN PATENT DOCUMENTS 148026 7/1985 European Pat. Off. .
3215409 10/1983 Fed. Rep. of Germany .
758168 10/1956 United Kingdom .

*Primary Examiner*—Richard L. Raymond
*Attorney, Agent, or Firm*—Edward McC. Roberts; Meredith C. Findlay

[57] ABSTRACT

The invention relates to novel heterocyclic organosilyl compounds of the general formula I

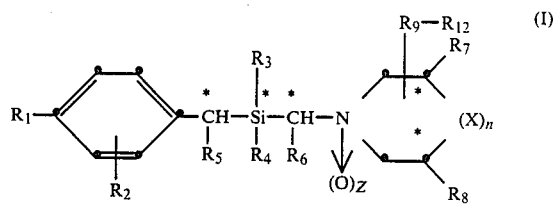

wherein
$R_1$ is hydrogen, $C_1$–$C_{10}$alkyl, $C_3$–$C_7$cycloalkyl, phenyl or trimethylsilyl,
$R_2$ is hydrogen or $C_1$–$C_4$alkyl, or
$R_1$ and $R_2$ together form a saturated or unsaturated ring containing 6 carbon atoms;
$R_3$ and $R_4$ are each independently of the other hydrogen, $C_1$–$C_4$alkyl or $C_1$–$C_4$alkoxy, and $R_4$ may also be $C_3$–$C_7$cycloalkyl;
$R_5$ to $R_{12}$ are each independently hydrogen or $C_1$–$C_4$alkyl, and
$R_8$ and $R_9$ together may also form a saturated or unsaturated ring containing 6 carbon atoms;
X is $CH_2$, oxygen or sulfur, and
n and Z are each independently of the other 0 or 1, and, if Z is 0, to the acid addition salts thereof.

The novel compounds have microbicidal properties and are suitable in particular for controlling phytopathogenic microorganisms.

24 Claims, No Drawings

MICROBICIDES

The present invention relates to novel heterocyclic organosilyl compounds of formula I below and to the acid addition salts thereof. The invention further relates to the preparation of these substances and to microbicidal compositions which contain, as active ingredient, at least one of these compounds. The invention also relates to the use of said compounds for controlling harmful microorganisms, in particular phytopathogenic fungi.

Specifically, the invention relates to compounds of formula I

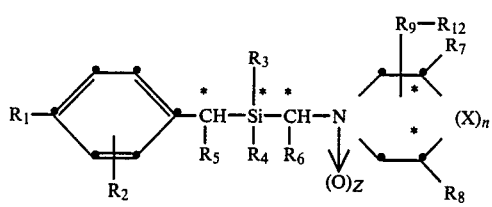

wherein
$R_1$ is hydrogen, $C_1$–$C_{10}$alkyl, $C_3$–$C_7$cycloalkyl, phenyl or trimethylsilyl,
$R_2$ is hydrogen or $C_1$–$C_4$alkyl, or
$R_1$ and $R_2$ together form a saturated or unsaturated ring containing 6 carbon atoms;
$R_3$ and $R_4$ are each independently of the other hydrogen, $C_1$–$C_4$alkyl or $C_1$–$C_4$alkoxy, and $R_4$ may also be $C_3$–$C_7$cycloalkyl;
$R_5$ to $R_{12}$ are each independently hydrogen or $C_1$–$C_4$alkyl, and
$R_8$ and $R_9$ together may also form a saturated or unsaturated ring containing 6 carbon atoms;
X is $CH_2$, oxygen or sulfur, and
n and Z are each independently of the other 0 or 1, and, if Z is 0, to the acid addition salts thereof.

Depending on the number of carbon atoms indicated, alkyl by itself or as moiety of another substituent will be understood as meaning for example the following groups: methyl, ethyl, propyl, butyl, pentyl, hexyl, heptyl, octyl, nonyl or decyl and the isomers thereof, e.g. isopropyl, isobutyl, tert-butyl, sec-butyl or isopentyl. $C_3$–$C_7$cycloalkyl is cyclopropyl, cyclobutyl, cyclopentyl, cyclohexyl or cycloheptyl. Acids suitable for the formation of salts of compounds of formula I wherein Z is 0 are all organic and inorganic acids provided they form phytophysiologically acceptable salts.

Examples of salt-forming acids are inorganic acids: hydrohalic acids such as hydrofluoric acid, hydrochloric acid, hydrobromic acid or hydriodic acid, as well as sulfuric acid, phosphoric acid, phosphorous acid and nitric acid; and organic acids such as acetic acid, trifluoroacetic acid, trichloroacetic acid, propionic acid, tartaric acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid or 2-acetoxybenzoic acid. These acids are added to the respective free compounds of formula I by methods which are known per se.

At room temperature the compounds of formula I are stable. They can be used in agriculture or related fields preventively or curatively for controlling phytopathogenic microorganisms. The compounds of formula I of the present invention are distinguished by a very good fungicidal activity in a wide range of concentrations, and their use poses no problems.

The compounds of formula I

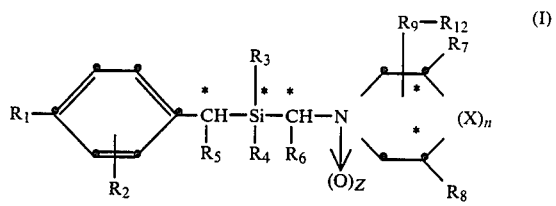

possess several centres of asymmetry (*). Dependent on substitution, in addition to those carbon atoms indicated, the silicon atom is also a possible centre of asymmetry (*). Contingent on the chiral groupings, the compounds of formula I may occur in various stereoisomeric forms containing enantiomeric or diastereoisomeric structures.

In general, the compounds of the invention are obtained in the form of a mixture of diastereoisomers or enantiomers. Said mixture can be resolved into the pure optical antipodes in conventional manner, e.g. by the fractional crystallisation of salts with optically active strong acids. However, it is also possible by selective synthesis to prepare pure diastereoisomeric or enantiomeric forms. The pure diastereoisomers and enantiomers may differ in their biological activity. For example, the one form may predominantly exhibit fungicidal activity on leaves and the other in the soil. Moreover, if the same spectrum of action is the same, a difference in the degree of activity may be observed.

The present invention relates to all pure enantiomers and diastereoisomers and to mixtures thereof with one another.

Compounds of formula I' below and, if Z is O, the acid addition salts thereof constitute a narrower scope of the invention:

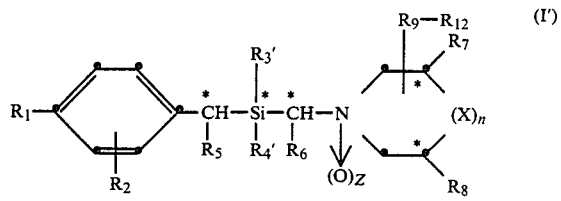

wherein
$R_1$ is hydrogen, $C_1$–$C_{10}$alkyl, $C_3$–$C_7$cycloalkyl, phenyl or trimethylsilyl,
$R_2$ hydrogen or $C_1$–$C_4$alkyl, or
$R_1$ and $R_2$ together form a saturated or unsaturated ring containing 6 carbon atoms;
$R_3'$, $R_4'$ and $R_5$ to $R_{12}$ are each independently hydrogen or $C_1$–$C_4$alkyl, and
$R_8$ and $R_9$ together may also form a saturated or unsaturated ring containing 6 carbon atoms;
X is $CH_2$, oxygen or sulfur, and
n and Z are each independently of the other 0 or 1.

On account of their pronounced microbicidal activity, the following groups of substances, including their acid addition salts, are preferred.

Group Ia:
Compounds of formula I' wherein
$R_1$ is $C_1$–$C_4$alkyl or trimethylsilyl, R₂ is hydrogen, methyl or ethyl, or
R₁ and R₂ together form a phenyl ring which is fused in the 3,4-position,
R₃' and R₄' are each independently of the other methyl or ethyl,
R₅, R₆, R₇ and R₈ are each independently hydrogen, methyl or ethyl,
R₉ to R₁₂ are each hydrogen, or
R₈ and R₉ together form a hexane or phenyl ring which is fused in the 3,4-position,
X is CH₂, oxygen or sulfur,
n is 0 or 1, and
Z is 0.

Group Ib:
Compounds of formula I' wherein
R₁ is isopropyl, tert-butyl or trimethylsilyl,
R₂ is hydrogen, or
R₁ and R₂ together form a phenyl ring which is fused in the 3,4-position,
R₃' and R₄' are each methyl,
R₅, R₆ and R₉ to R₁₂ are each hydrogen,
R₇ and R₈ are each independently of the other hydrogen or methyl, or
R₈ and R₉ together form a hexane or phenyl ring which is fused in the 3,4-position,
X is CH₂, oxygen or sulfur,
n is 0 or 1, and
Z is 0.

Group Ic:
Compounds of formula I' wherein
R₁ is isopropyl, tert-butyl or trimethylsilyl,
R₂ is hydrogen, or
R₁ and R₂ together form a phenyl ring which is fused in the 3,4-position,
R₃' and R₄' are each methyl,
R₅, R₆ and R₉ to R₁₂ are each hydrogen,
R₇ and R₈ are each independently of the other hydrogen or methyl, or
R₈ and R₉ together form a hexane or phenyl ring which is fused in the 3,4-position,
X is CH₂, oxygen or sulfur,
n is 1, and
Z is 0.

Group Id:
Compounds of formula I wherein
R₁ is C₁-C₄alkyl or trimethylsilyl,
R₂ is hydrogen, methyl or ethyl, or
R₁ and R₂ together form a phenyl ring which is fused in the 3,4-position,
R₃ and R₄ are each independently of the other methyl, ethyl, methoxy or cyclohexyl,
R₅, R₆, R₇ and R₈ are each independently hydrogen, methyl or ethyl,
R₉ to R₁₂ are each hydrogen, or
R₈ and R₉ together form a hexane or phenyl ring which is fused in the 3,4-position,
X is CH₂, oxygen or sulfur,
n is 0 or 1, and Z is 0.

Preferred individual compounds are:
Group A:
dimethyl-4-tert-butylbenzyl-2,6-dimethylmorpholin-(4)-ylmethylsilane (comp. 1.1);
dimethyl-4-tert-butylbenzylmorpholin-(4)-ylmethylsilane (comp. 1.5);
dimethyl-4-tert-butylbenzyl-N-piperidinylmethylsilane (comp. 1.6);
dimethyl-4-trimethylsilylbenzyl-N-piperidinylmethylsilane (comp. 1.15);
dimethyl-4-trimethylsilylbenzylmorpholin-(4)-ylmethylsilane (comp. 1.16);
dimethyl-4-trimethylsilylbenzyl-2,6-dimethylmorpholin-(4)-ylmethylsilane (comp. 1.17);
dimethyl-4-tert-butylbenzyltetrahydro-1,4-thiazin-(4)-ylmethylsilane (comp. 1.28);
dimethyl-4-isopropylbenzyltetrahydro-1,4-thiazin-(4)-ylmethylsilane (comp. 1.29);
dimethyl-4-tert-butylbenzyl-N-pyrrolidinylmethylsilane (comp. 1.30);
dimethyl-4-trimethylsilylbenzyltetrahydro-1,4-thiazin-(4)-ylmethylsilane (comp. 1.33);
dimethyl-4-tert-butylbenzylcyclohexa[c]piperidin-(1)-ylmethylsilane (comp. 2.4);
dimethyl-4-tert-butylbenzylbenzo[c]piperidin-(1)-ylmethylsilane (comp. 2.5);
dimethyl-4-trimethylsilylbenzylcyclohexa[c]piperidin-(1)-ylmethylsilane (comp. 2.14);
dimethylnaphthyl-(2)-ylmethyl-2,6-dimethylmorpholin-(4)-ylmethylsilane (comp. 3.1);
dimethylnaphthyl-(2)-ylmethylcyclohexa[c]piperidin-(1)-ylmethylsilane (Verb. 3.8).

Group B:
cis-dimethyl-4-tert-butylbenzyl-2,6-dimethylmorpholin-4-ylmethylsilane (comp. 1.37);
cis-cyclohexyl-4-tert-butylbenzyl-2,6-dimethylmorpholin-4-ylmethylsilane (comp. 1.44);
cis-methoxycyclohexyl-(4-tert-butylbenzyl)-2,6-dimethylmorpholin-(4)-ylsilane (comp. 1.46).

The novel compounds are furmula I are prepared by
(1) in a multistage process
(a) reacting a compound of formula II

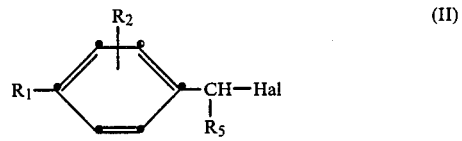 (II)

with an alkaline earth metal, preferably magnesium, and
(b) reacting the resultant organometallic compound of formula III

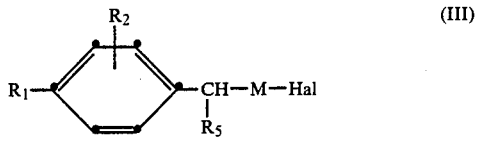 (III)

with a halosilane compound of formula IV

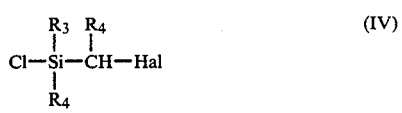 (IV)

and
(c) reacting the resultant compound of formula V

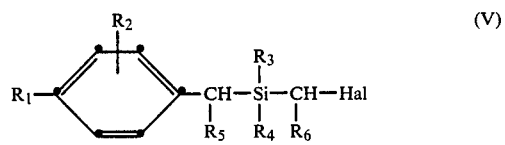 (V)

with a heterocyclic amine of formula VI

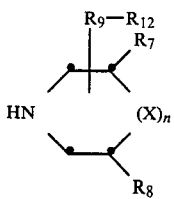

(VI)

in the absence or presence of an auxiliary base, to give a compound of formula Ia

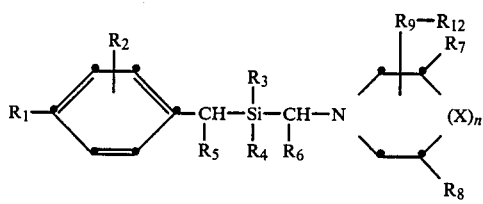

(Ia)

and, if desired, (d) converting the resultant compound of formula Ia into the compound of formula Ib

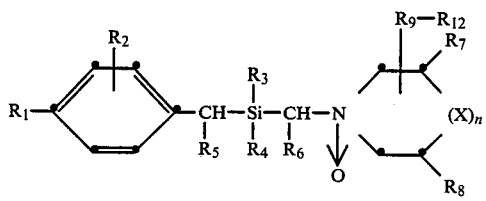

(Ib)

by oxidation with an oxidising agent such as $H_2O_2$ or a peracid;
or (2) reacting an organometallic compound of formula VII

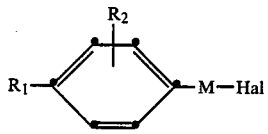

(VII)

with an organic silicone compound of formula VIII

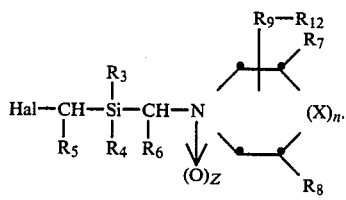

(VIII)

In the above formulae II to VIII the radicals $R_1$ to $R_{12}$ and the symbols n and Z are as defined for formula I, M is an alkaline earth metal atom, preferably magnesium, and Hal is halogen, preferably chlorine, bromine or iodine.

The reaction temperatures in process variant (1) are in the range from −80° to 80° C., preferably from −20° to 80° C., in step (1a); from −20° to 100° C., preferably from 0° to 40° C., in step (1b); from 0° to 180° C., preferably from 20° to 150° C., in step (1c); and from 0° to 100° C., preferably from 0° to 50° C., in step (1d). The reaction temperatures in process variant (2) are in the range from −20° to 80° C., preferably from 0° to 60° C.

Process steps (1a) and (1b) can be advantageously performed in a single reaction vessel, thereby making it unnecessary to isolate and purify the product of formula V.

The auxiliary bases employed in process step (1c) act as acid acceptors. For this purpose it is possible to use any acid acceptors conventionally employed in the art, for example tertiary amines and alkali metal and alkaline earth metal compounds. Examples of such acid acceptors are the hydroxides, oxides and carbonates of lithium, sodium, potassium, magnesium, calcium and barium, and also further basic compounds such as trimethylamine, triethylamine, tripropylamine, tributylamine, tribenzylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylpyrrolidine, N-methylimidazole, N-methylpyrrole, N-methylmorpholine, N-methylhexamethyleneimine, pyridine, quinoline, α-picoline, β-picoline, isoquinoline, pyrimidine, acridine, N,N,N',N'-tetramethylethylenediamine, N,N,N',N'-tetraethylethylenediamine, quinoxaline, N-propyldiisopropylamine, N,N-dimethylcyclohexylamine, 2,6-lutidine, 2,4-lutidine, triethylenediamine.

It is convenient to employ the acid acceptor in an amount of up to 20% more than or less than the equivalent amount, based on the starting material.

Contingent on the respective reaction conditions, inert solvents and diluents are employed in the processes of the present invention. Examples of suitable solvents and diluents are: halogenated hydrocarbons, in particular chlorinated hydrocarbons such as tetrachloroethylene, tetrachloroethane, dichloropropane, methylene chloride, dichlorobutane, chloroform, chloronaphthalene, dichloronaphthalene, carbon tetrachloride, trichloroethane, trichloroethylene, pentachloroethane, difluorobenzene, 1,2-dichloroethane, 1,1-dichloroethane, 1,2-cis-dichloroethylene, chlorobenzene, fluorobenzene, bromobenzene, iodobenzene, dichlorobenzene, dibromobenzene, chlorotoluene, trichlorobenzene; ethers such as ethyl propyl ether, methyl tert-butyl ether, n-butyl ethyl ether, di-n-butyl ether, diisobutyl ether, diisoamyl ether, diisopropyl ether, anisol, phenetole, cyclohexyl methyl ether, diethyl ether, ethylene glycol dimethyl ether, tetrahydrofuran, dioxane, thioanisole, dichlorodiethyl ether; nitrohydrocarbons such as nitromethane, nitroethane, nitrobenzene, chloronitrobenzene, o-nitrotoluene; nitriles such as acetonitrile, butyronitrile, isobutyronitrile, benzonitrile, m-chlorobenzonitrile; aliphatic or cycloaliphatic hydrocarbons such as heptane, pinane, nonane, cymene, petrol fractions within a boiling point interval of 70° to 190° C., cyclohexane, methylcyclohexane, decalin, petroleum ether, hexane, ligroin, trimethylpentane, trimethylpentane, 2,3,3-trimethylpentane, octane; esters such as ethyl acetate, ethyl acetoacetate, isobutyl acetate; amides, e.g. formamide, methylformamide, dimethylformamide; ketones such as acetone, methyl ethyl ketone, and, optionally, water. Mixtures of said solvents and diluents may also be employed.

The salts of compounds of formula I wherein Z is 0 are obtained by adding the respective acid to the free amine, if appropriate in an inert solvent, in which case the solvent is subsequently distilled off, and if necessary, recrystallising the resultant residue.

Processes for the preparation of fungicidal heterocyclic organosilyl compounds are described in German Offenlegungsschrift No. 32 15 409 and in published European patent application No. 148 026. However, the fungicidal activity of these compounds has not always proved entirely satisfactory, especially when employed at low concentrations.

Surprisingly, it has been found that the compounds of formula I of this invention have, for practical field application purposes, a very advantageous microbicidal spectrum against phytopathogenic fungi and bacteria. Compounds of formula I have very advantageous curative, systemic and, in particular, preventive properties, and can be used for protecting numerous cultivated plants. With the compounds of formula I it is possible to inhibit or destroy the microorganisms which occur in plants or in parts of plants (fruit, blossoms, leaves, stems, tubers, roots) in different crops of useful plants, while at the same time the parts of plants which grow later are also protected from attack by such microorganisms, e.g. fungi.

As microbicides, the compounds of formula I are effective e.g. against the phytopathogenic fungi belonging to the following classes: *Fungi imperfecti* (e.g. Botrytis, Helminthosporium, Fusarium, Septoria, Cercospora and Alternaria); Basidiomycetes (e.g. the genera Hemileia, Rhizocotonia, Puccinia); and, in particular, against the class of the Ascomycetes (e.g. Venturia, Podosphaera, Erysiphe, Monilinia, Uncinula). In addition, the compounds of formula I have a systemic action. They can also be used as dressing agents for protecting seeds (fruit, tubers, grains) and plant cuttings aginst fungus infections as well as against phytopathogenic fungi which occur in the soil.

Accordingly, the invention also relates to pesticidal compositions, in particular to microbicidal compositions, as well as to the use thereof in agriculture and related fields.

The invention further embraces the preparation of these compositions, which comprises homogeneously mixing the active ingredient with one or more compounds or groups of compounds described herein. The invention furthermore relates to a method of treating plants, which comprises applying thereto the compounds of formula I or the novel compositions.

Target crops to be protected within the scope of the present invention comprise e.g. the following species of plants: cereals (wheat, barley, rye, oats, rice, sorghum and related crops), beet (sugar beet and fodder beet), pomes, drupes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconut, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (composites).

The compounds of formula I are normally applied in the form of compositions and can be applied to the crop area or plant to be treated, simultaneously or in succession, with further compounds. These compounds can be both fertilisers or micronutrient donors or other preparations that influence plant growth. They can also be selective herbicides, insecticides, fungicides, bactericides, nematicides, mollusicides or mixtures of several of these preparations, if desired together with further carriers, surfactants or application promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a compound of formula I, or an agrochemical composition which contains at least one of said compounds, is foliar application. The number of applications and the rate of application depend on the risk of infestation by the corresponding pathogen (species of fungus). However, the compounds of formula I can also penetrate the plant through the roots via the soil (systemic action) by empregnating the locus of the plant with a liquid formulation, or by applying the compounds in solid form to the soil, e.g. in granular form (soil application). The compounds of formula I may also be applied to seeds (coating) either by impregnating the seeds with a liquid formulation containing a compound of formula I, or coating them with a solid formulation. In special cases, further types of application are also possible, e.g. selective treatment of the plant stems or buds.

The compounds of formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues. Particularly advantageous application promoting adjuvants which are able to reduce substantially the rate of application are also natural (animal or vegetable) or synthetic phospholipids of the series of the cephalins and lecithins, which can be obtained e.g. from soybeans.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially alkanesulfonates, fatty alcohol sulfates, sulfonated benzimidazole derivatives or alkylsulfonates.

The fatty alcohol sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethyleneethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

Further surfactants customarily employed in the art of formulation are either known to the skilled person or they can be found in the relevant literature.

The agrochemical compositions usually contain 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also contain further auxiliaries such as stabilisers, antifoams, viscosity regulators, binders, tackifiers as well as fertilisers or other active ingredients for obtaining special effects.

Agrochemical compositions containing compounds of formula I as active ingredients likewise constitute an object of the present invention.

The invention is illustrated in more detail by the following non-limitative Examples.

1. PREPARATORY EXAMPLES

Example 1.1

Preparation of

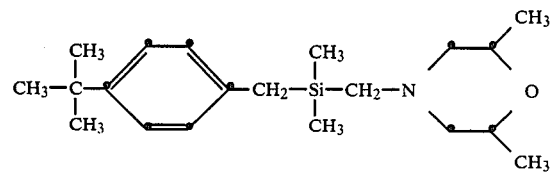

Dimethyl-4-tert-butylbenzyl-2,6-dimethylmorpholin-(4)-ylmethylsilane 7.6 g (0.03M) of dimethyl-4-tert-butylbenzyl-chloromethylsilane and 20 ml of 2,6-dimethylmorpholine are stirred overnight at 150° C. After cooling, the reaction mixture is dissolved in 100 ml of methylene chloride, and the resultant solution is washed three times with water and once with a saturated solution of potassium carbonate. The batch is dried over sodium sulfate and filtered, and the filtrate is concentrated. The crude product so obtained is distilled under a high vacuum, affording 2.7 g of the title compound with a boiling point of 100°–102° C./1.3 pa.

Preparation of the intermediate

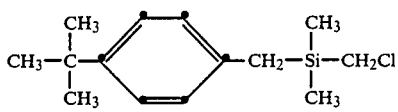

Dimethyl-4-tert-butylbenzylchloromethylsilane 1.2 g (0.05M) of magnesium shavings are charged into 20 ml of diethyl ether. After the addition of about 1 ml of 4-tert-butylbenzyl chloride, the batch is heated to boiling point and a number of iodine crsytals are added. After the onset of the reaction, the rest of the 4-tert-butylbenzyl chloride (a total of 10 g [0.055M] in 80 ml of diethyl ether) is added dropwise such that the temperature is kept at 25°–30° C. The reaction mixture is stirred further for 2 hours at room temperature. 7.2 g (0.05M) of chloromethyldimethylchlorosilane in 20 ml of diethyl ether are then added dropwise at room temperature, and the mixture is stirred further overnight at room temperature. With ice cooling, 100 ml of a saturated solution of ammonium chloride are added to the reaction mixture, and the organic phase is separated, diluted with ethyl acetoacetate and washed three times with water. The batch is dried over sodium sulfate and filtered, and the filtrate is concentrated under a water jet vacuum. The crude intermediate so obtained is cooled to 0° C. and filtered, affording 11.2 g (88% of theory) of the desired intermediate as filtrate. For further purification, the product can be distilled under a water jet vacuum (boiling point: 149°–150° C./2000 Pa).

The following compounds can be prepared by the procedure described in the foregoing Example or by one of the methods indicated for the synthesis of compounds of formula I:

TABLE 1

| Comp. | $R_1$ | $R_2$ | $R_3$ | $R_4$ | $R_5$ | $R_6$ | $R_7$ | $R_8$ | X | Physical data |
|---|---|---|---|---|---|---|---|---|---|---|
| 1.1 | $C_4H_9(t)$ | H | $CH_3$ | $CH_3$ | H | H | $CH_3$ | $CH_3$ | O | b.p. 100–102° C. (1.3 Pa) |
| 1.2 | $C_4H_9(t)$ | H | $C_2H_5$ | $C_2H_5$ | H | H | $CH_3$ | $CH_3$ | O | |
| 1.3 | $C_4H_9(t)$ | H | $CH_3$ | $CH_3$ | $CH_3$ | H | $CH_3$ | $CH_3$ | O | |
| 1.4 | $C_4H_9(t)$ | H | $CH_3$ | $CH_3$ | H | $CH_3$ | $CH_3$ | $CH_3$ | O | |
| 1.5 | $C_4H_9(t)$ | H | $CH_3$ | $CH_3$ | H | H | H | H | O | b.p. 107–108° C. (4.0 Pa) |
| 1.6 | $C_4H_9$ | H | $CH_3$ | $CH_3$ | H | H | H | H | $CH_2$ | b.p. 92–95° C. (0.7 Pa) |
| 1.7 | $C_4H_9(t)$ | H | $C_2H_5$ | $C_2H_5$ | H | H | H | H | $CH_2$ | |
| 1.8 | $CH_3$ | $CH_3$ | $CH_3$ | $CH_3$ | H | H | $CH_3$ | $CH_3$ | O | |
| 1.9 | $C_3H_7(i)$ | H | $CH_3$ | $CH_3$ | H | H | $CH_3$ | $CH_3$ | O | |
| 1.10 | $C_3H_7(i)$ | H | $CH_3$ | $CH_3$ | H | H | H | H | O | |
| 1.11 | $C_3H_7(i)$ | H | $CH_3$ | $CH_3$ | H | H | H | H | $CH_2$ | |
| 1.12 | $C_3H_7(i)$ | H | $CH_3$ | $CH_3$ | $CH_3$ | H | $CH_3$ | $CH_3$ | O | |
| 1.13 | $C_2H_5$ | H | $CH_3$ | $CH_3$ | H | H | $CH_3$ | $CH_3$ | O | |
| 1.14 | $C_2H_5$ | H | $CH_3$ | $CH_3$ | H | H | H | H | $CH_2$ | |
| 1.15 | $(CH_3)_3Si-$ | H | $CH_3$ | $CH_3$ | H | H | H | H | $CH_2$ | b.p. 96–98° C. (1.3 Pa) |
| 1.16 | $(CH_3)_3Si-$ | H | $CH_3$ | $CH_3$ | H | H | H | H | O | b.p. 104–108° C. (2.6 Pa) |
| 1.17 | $(CH_3)_3Si-$ | H | $CH_3$ | $CH_3$ | H | H | $CH_3$ | $CH_3$ | O | b.p. 100–102° C. (2.6 Pa) |
| 1.18 | $(CH_3)_3Si-$ | H | $C_2H_5$ | $C_2H_5$ | H | H | $CH_3$ | $CH_3$ | O | |
| 1.19 | $(CH_3)_3Si-$ | H | $CH_3$ | $CH_3$ | $CH_3$ | H | $CH_3$ | $CH_3$ | O | |
| 1.20 | $C_4H_9(t)$ | H | $CH_3$ | $CH_3$ | $CH_3$ | $CH_3$ | $CH_3$ | $CH_3$ | O | |
| 1.21 | $C_3H_7(i)$ | H | $CH_3$ | $CH_3$ | $CH_3$ | $CH_3$ | $CH_3$ | $CH_3$ | O | |
| 1.22 | $C_3H_7(i)$ | H | $CH_3$ | $CH_3$ | $CH_3$ | $CH_3$ | H | H | $CH_2$ | |
| 1.23 | $C_4H_9(t)$ | H | $CH_3$ | $CH_3$ | $CH_3$ | $CH_3$ | H | H | $CH_2$ | |
| 1.24 | (cyclopropyl) | H | $CH_3$ | $CH_3$ | H | H | $CH_3$ | $CH_3$ | O | |
| 1.25 | (cyclopropyl) | H | $CH_3$ | $CH_3$ | H | H | H | H | $CH_2$ | |
| 1.26 | (phenyl) | H | $CH_3$ | $CH_3$ | H | H | $CH_3$ | $CH_3$ | O | |

TABLE 1-continued

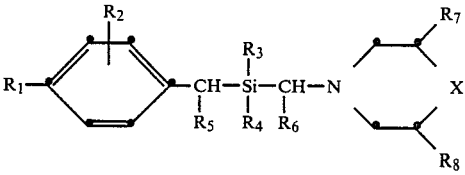

| Comp. | $R_1$ | $R_2$ | $R_3$ | $R_4$ | $R_5$ | $R_6$ | $R_7$ | $R_8$ | X | Physical data |
|---|---|---|---|---|---|---|---|---|---|---|
| 1.27 | 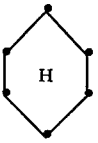 | H | $CH_3$ | $CH_3$ | H | H | H | H | $CH_2$ | |
| 1.28 | $C_4H_9(t)$ | H | $CH_3$ | $CH_3$ | H | H | H | H | S | b.p. 127–130° C. (1.3 Pa) |
| 1.29 | $C_3H_7(i)$ | H | $CH_3$ | $CH_3$ | H | H | H | H | S | |
| 1.30 | $C_4H_9(t)$ | H | $CH_3$ | $CH_3$ | H | H | H | H | — | b.p. 88–90° C. (2.7 Pa) |
| 1.31 | $C_3H_7(i)$ | H | $CH_3$ | $CH_3$ | H | H | H | H | — | |
| 1.32 | $(CH_3)_3Si$ | H | $CH_3$ | $CH_3$ | H | H | H | H | — | |
| 1.33 | $(CH_3)_3Si$ | H | $CH_3$ | $CH_3$ | H | H | H | H | S | b.p. 120–128° C. (3.0 Pa) |
| 1.34 | $C_4H_9(t)$ | H | $C_2H_5$ | $C_2H_5$ | H | H | H | H | S | |
| 1.35 | $C_4H_9(t)$ | H | $C_2H_5$ | $C_2H_5$ | H | H | H | H | O | |
| 1.36 | $C_4H_9(t)$ | H | $C_2H_5$ | $C_2H_5$ | H | H | H | H | — | |
| 1.37 | $C_4H_9(t)$ | H | $CH_3$ | $CH_3$ | H | H | $CH_3$* | $CH_3$* | O | b.p. 120–125° C. (11.7 Pa) |
| 1.38 | $(CH_3)_3Si$ | H | $CH_3$ | $CH_3$ | H | H | $CH_3$* | $CH_3$* | O | |
| 1.39 | $C_4H_9(t)$ | H | H | $CH_3$ | H | H | $CH_3$ | $CH_3$ | O | |
| 1.40 | $C_4H_9(t)$ | H | H | $CH_3$ | H | H | H | H | $CH_2$ | |
| 1.41 | $C_4H_9(t)$ | H | H | $CH_3$ | H | H | $CH_3$* | $CH_3$* | O | |
| 1.42 | $C_4H_9(t)$ | H | H | 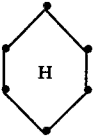 | H | H | H | H | $CH_2$ | |
| 1.43 | $C_4H_9(t)$ | H | H | 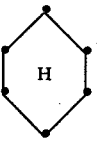 | H | H | $CH_3$ | $CH_3$ | O | |
| 1.44 | $C_4H_9(t)$ | H | H | 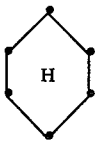 | H | H | $CH_3$* | $CH_3$* | O | |
| 1.45 | $C_4H_9(t)$ | H | $OCH_3$ | 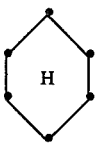 | H | H | $CH_3$ | $CH_3$ | O | |
| 1.46 | $C_4H_9(t)$ | H | $OCH_3$ |  | H | H | $CH_3$* | $CH_3$* | O | |
| 1.47 | $C_4H_9(t)$ | H | $OCH_3$ | $OCH_3$ | H | H | $CH_3$ | $CH_3$ | O | |
| 1.48 | $C_4H_9(t)$ | H | $OCH_3$ | $OCH_3$ | H | H | $CH_3$* | $CH_3$* | O | |
| 1.49 | $C_4H_9(t)$ | H | $OCH_3$ | $OCH_3$ | H | H | H | H | $CH_2$ | |

*CIS-isomer

TABLE 2

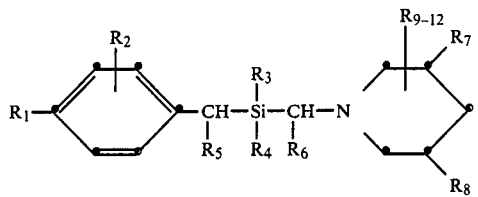

| Comp. | R1 | R2 | R3 | R4 | R5 | R6 | R7 | R8 | R9 | R10 | R11 | R12 | Physical data |
|---|---|---|---|---|---|---|---|---|---|---|---|---|---|
| 2.1 | $C_4H_9(t)$ | H | $CH_3$ | $CH_3$ | H | H | H | H | 2-$CH_3$ | 6-$CH_3$ | H | H | b.p. 110–115° C. (2.6 Pa) |
| 2.2 | $C_4H_9(t)$ | H | $CH_3$ | $CH_3$ | H | H | H | H | 2-$CH_3$ | 6-$CH_3$ | 2-$CH_3$ | 6-$CH_3$ | |
| 2.3 | $C_4H_9(t)$ | H | $CH_3$ | $CH_3$ | H | H | H | 3-$CH_3$ | 3-$CH_3$ | H | H | H | b.p. 110–114° C. (5.0 Pa) |
| 2.4 | $C_4H_9(t)$ | H | $CH_3$ | $CH_3$ | H | H | H | 3-$(CH_2)_4$—4 | | H | H | H | b.p. 145–149° C. (5.0 Pa) |
| 2.5 | $C_4H_9(t)$ | H | $CH_3$ | $CH_3$ | H | H | H | 3-$(CH)_4$—4* | | H | H | H | b.p. 175–181° C. (2.5 Pa) |
| 2.6 | $C_3H_7(i)$ | H | $CH_3$ | $CH_3$ | H | H | H | H | 2-$CH_3$ | 6-$CH_3$ | H | H | |
| 2.7 | $C_3H_7(i)$ | H | $CH_3$ | $CH_3$ | H | H | H | H | 2-$CH_3$ | 6-$CH_3$ | 2-$CH_3$ | 6-$CH_3$ | |
| 2.8 | $C_3H_7(i)$ | H | $CH_3$ | $CH_3$ | H | H | H | 3-$CH_3$ | 3-$CH_3$ | H | H | H | |
| 2.9 | $C_3H_7(i)$ | H | $CH_3$ | $CH_3$ | H | H | H | 3-$(CH_2)_4$—4 | | H | H | H | |
| 2.10 | $C_3H_7(i)$ | H | $CH_3$ | $CH_3$ | H | H | H | 3-$(CH)_4$—4* | | H | H | H | |
| 2.11 | $C_4H_9(t)$ | H | H | (cyclohexyl) | H | H | H | 3-$(CH_2)_4$—4 | | H | H | H | |
| 2.12 | $(CH_3)_3Si$ | H | $CH_3$ | $CH_3$ | H | H | H | H | 2-$CH_3$ | 6-$CH_3$ | H | H | |
| 2.13 | $(CH_3)_3Si$ | H | $CH_3$ | $CH_3$ | H | H | H | H | 2-$CH_3$ | 6-$CH_3$ | 2-$CH_3$ | 6-$CH_3$ | |
| 2.14 | $(CH_3)_3Si$ | H | $CH_3$ | $CH_3$ | H | H | H | 3-$CH_3$ | 3-$CH_3$ | H | H | H | |
| 2.15 | $(CH_3)_3Si$ | H | $CH_3$ | $CH_3$ | H | H | H | 3-$(CH_2)_4$—4 | | H | H | H | b.p. 143–146° C. (2.6 Pa) |
| 2.16 | $(CH_3)_3Si$ | H | $CH_3$ | $CH_3$ | H | H | H | 3-$(CH)_4$—4* | | H | H | H | |
| 2.17 | $C_4H_9(t)$ | H | $C_2H_5$ | $C_2H_5$ | H | H | H | 3-$(CH)_4$—4* | | H | H | H | |
| 2.18 | $C_4H_9(t)$ | H | $CH_3$ | $CH_3$ | $CH_3$ | H | H | 3-$(CH)_4$—4* | | H | H | H | |
| 2.19 | $C_4H_9(t)$ | H | $CH_3$ | $CH_3$ | $CH_3$ | $CH_3$ | H | 3-$(CH)_4$—4* | | H | H | H | |
| 2.20 | $C_4H_9(t)$ | H | $C_2H_5$ | $C_2H_5$ | H | H | H | 3-$(CH_2)_4$—4 | | H | H | H | |
| 2.21 | $C_4H_9(t)$ | H | $CH_3$ | $CH_3$ | $CH_3$ | H | H | 3-$(CH_2)_4$—4 | | H | H | H | |
| 2.22 | $C_4H_9(t)$ | H | $CH_3$ | $CH_3$ | $CH_3$ | $CH_3$ | H | 3-$(CH_2)_4$—4 | | H | H | H | |
| 2.23 | $C_4H_9(t)$ | H | $CH_3$ | $CH_3$ | $CH_3$ | H | H | 3-$CH_3$ | 3-$CH_3$ | H | H | H | |
| 2.24 | $C_4H_9(t)$ | H | $C_2H_5$ | $C_2H_5$ | H | H | H | 3-$CH_3$ | 3-$CH_3$ | H | H | H | |

*$(CH)_4$ = benzo

TABLE 3

Structure: naphthyl-CH₂-Si(CH₃)₂-CH₂-R

| Comp. | R | Physical data |
|---|---|---|
| 3.1 | morpholine with 2,6-dimethyl (−N with O, two CH₃) | b.p. 144–150° C./2.6 Pa |
| 3.2 | morpholine (−N−O ring) | b.p. 138–140° C./1.3 Pa |
| 3.3 | thiomorpholine (−N−S ring) | b.p. 158–162° C./2.6 Pa |
| 3.4 | piperidine (−N 6-ring) | b.p. 138–142° C./1.3 Pa |
| 3.5 | pyrrolidine (−N 5-ring) | b.p. 134–137° C./2.6 Pa |
| 3.6 | 4,4-dimethylpiperidine | b.p. 138–140° C./2.6 Pa |
| 3.7 | 3,5-dimethylpiperidine | |
| 3.8 | 1,2,3,4-tetrahydroquinoline | b.p. 184–188° C./7.8 Pa |
| 3.9 | indoline | |

TABLE 3-continued

| Comp. | R | Physical data |
|---|---|---|
| 3.10 | cis-2,6-dimethylmorpholine | |

2. Formulation Examples for liquid active ingredients of formula I (throughout, percentages are by weight)

2.1. Emulsifiable concentrates

| | (a) | (b) | (c) |
|---|---|---|---|
| a compound of Tables 1 to 3 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

2.2. Solutions

| | (a) | (b) | (c) | (d) |
|---|---|---|---|---|
| a compound of Tables 1 to 3 | 80% | 10% | 5% | 95% |
| ethylene glycol monomethyl ether | 20% | — | — | — |
| polyethylene glycol (mol. wt. 400) | — | 70% | — | — |
| N—methyl-2-pyrrolidone | — | 20% | — | — |
| epoxidised coconut oil | — | — | 1% | 5% |
| petroleum distillate (boiling range 160–190° C.) | — | — | 94% | — |

These solutions are suitable for application in the form of microdrops.

2.3. Granulates

| | (a) | (b) |
|---|---|---|
| a compound of Tables 1 to 3 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

2.4. Dusts

| | (a) | (b) |
|---|---|---|
| a compound of Tables 1 to 3 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Formulation Examples for solid active ingredients of formula I (throughout, percentages are by weight)

| 2.5. Wettable powders | (a) | (b) | (c) |
|---|---|---|---|
| a compound of Tables 1 to 3 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.6. Emulsifiable concentrate | |
|---|---|
| a compound of Tables 1 to 3 | 10% |
| octylphenol polyethlene glycol ether (4–5 moles of ethylene oxide) | 3% |
| calcium dodecylbenzenesulfonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

| 2.7. Dusts | (a) | (b) |
|---|---|---|
| a compound of Tables 1 to 3 | 5% | 8% |
| talcum | 95% | — |
| kaolin | — | 92% |

Ready-for-use dusts are obtained by mixing the active ingredient with the carrier, and grinding the mixture in a suitable mill.

| 2.8. Extruder granulate | |
|---|---|
| a compound of Tables 1 to 3 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.9. Coated granulate | |
|---|---|
| a compound of Tables 1 to 3 | 3% |
| polyethylene glycol (mol. wt. 200) | 3% |
| kaolin | 94% |

The finely ground active ingredient is uniformly applied, in a mixer, to the kaolin moistened with polyethlene glycol. Non-dusty coated granulates are obtained in this manner.

| 2.10. Suspension concentrate | |
|---|---|
| a compound of Tables 1 to 3 | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

3. Biological Examples

Example 3.1.

Action against *Puccinia graminis* on wheat (a) Residual-protective action

Wheat plants are treated 6 days after sowing with a spray mixture (0.02% active ingredient) prepared from a wettable powder formulation of the test compound. After 24 hours the treated plants are infected with a uredospore suspension of the fungus. The infected plants are incubated for 48 hours at 95–100% relative humidity and about 20° C. and then stood in a greenhouse at about 22° C. Evaluation of rust pustule development is made 12 days after infection.

(b) Systemic action

Wheat plants are treated 5 days after sowing with a spray mixture (0.006% active ingredient, based on the volume of the soil) prepared from a wettable powder formulation of the test compound. After 48 hours the treated plants are infected with a uredospore suspension of the fungus. The plants are then incubated for 48 hours at 95–100% relative humidity and about 20° C. and then stood in a greenhouse at about 22° C. Evaluation or rust pustule development is made 12 days after infection.

Compounds of the Tables exhibit good activity against Puccinia fungi. On the other hand, Puccinia attack is 100% on untreated and infected control plants. Thus e.g. compounds 1.1; 1.6; 1.7; 1.17; 1.28; 2.3; 2.4; 3.3 and 3.5 reduce Puccinia attack to less than 20%.

Example 3.2.

Action against *Cercospora arachidicola* on groundnut plants

Residual protective action

Groundnut plants 10–15 cm in height are sprayed with a spray mixture (0.02% active ingredient) prepared from a wettable powder formulation of the test compound, and infected 48 hours later with a conidia suspension of the fungus. The infected plants are incubated for 72 hours at about 21° C. and high humidity and then stood in a greenhouse until the typical leaf specks occur. Evaluation of the fungicidal action is made 12 days after infection and is based on the number and size of the specks.

Compared with untreated and infected control plants (number and size of the specks=100%), Cercospora attack on groundnut plants treated with compounds of the Tables is substantially reduced. Thus e.g. compounds 1.1; 1.5; 1.6; 1.16; 1.17; 2.3; 2.4; 2.14 and 3.5 inhibit the occurrence of specks almost completely (0 to 10%) in the above test.

Example 3.3.

Action against *Erysiphe graminis* on barley (a) Residual protective action

Barley plants about 8 cm in height are sprayed with a spray mixture (0.02% active ingredient) prepared from a wettable powder formulation of the test compound. The treated plants are dusted with conidia of the fungus after 3 to 4 hours. The infected barley plants are stood in a greenhouse at about 22° C. The fungus attack is evaluated after 10 days.

(b) Systemic action

A spray mixture (0.006% active ingredient, based on the volume of the soil) prepared from a wettable powder formulation of the test compound is poured onto barley plants about 8 cm in height. Care is taken that the spray mixture does not come into contact with the parts of the plants above the soil. The treated plants are infected 48 hours later with a conidia suspension of the fungus. The infected barley plants are then stood in a greenhouse at about 22° C. and evaluation of infestation is made after 10 days.

Compounds of the Tables exhibit good activity against Erysiphe fungi. On the other hand, Erysiphe attack is 100% on untreated and infected control plants. Thus e.g. compounds 1.1; 1.5; 1.6; 1.15; 1.16; 1.17; 1.28; 1.30; 1.33; 2.1; 2.3; 2.4; 2.5; 2.14; 3.1; 3.5; 3.6 and 3.8 inhibit fungus attack on barley to 0 to 5%.

Example 3.4.

Action against *Botyrtis cinerea* on apples

Artificially damaged apples are treated by dropping a spray mixture prepared from a wettable powder formulation of the test compound onto the injury sites. The treated fruit is then inoculated with a spore suspension of Botrytis cinerea and incubated for 1 week at high humidity and about 20° C.

Evaluation is made by counting the number of injury sites attacked by rot and deducing the fungicidal action of the test compound therefrom. Compared with untreated controls, compounds 1.1; 1.5; 1.16; 1.17; 1.28; 2.4; 2.14; 3.9 and other inhibit fungus attack almost completely (0 to 5%).

Example 3.5.

Action against *Pyricularia oryzae* on rice plants (a) Residual protective action After a cultivation period of 2 weeks, rice plants are sprayed with a spray mixture (0.05% active ingredient) prepared from a wettable powder formulation of the test compound. After 48 hours the treated plants are infected with a conidia suspension of the fungus. Evaluation of fungus attack is made after incubation for 5 days at 95–100% relative humidity and 24° C.

(b) Systemic action

A spray mixture (0.006% active ingredient, based on the volume of the soil) prepared from a wettable powder formulation of the test compound is poured onto two-week-old rice plants growing in earthenware pots normally used for flowers. The pots are then filled with water until the lowermost stem parts of the rice plants are standing in water. After 48 hours the treated rice plants are infected with a conidia suspension of the fungus. Evaluation of fungus attack is made after incubation of the infected plants for 5 days at 95 to 100% relative humidity and about 24° C.

Compounds of the Tables exhibit good activity against the Pyricularia fungus. On the other hand, Pyricularia attack on untreated and infected control plants is 100%. Thus e.g. compounds 1.16 and 2.3 inhibit fungus attack to 0 to 5%.

Example 3.6.

Action against *Rhizoctonia solani* (soil fungus) on rice plants (a) Protective local soil application A spray mixture (0.006% active ingredient) prepared from a formulation of the test compound is poured onto 12-day-old rice plants without contaminating the parts of the plants above the soil. In order to infect the treated plants, a suspension of mycelium and sclerotia of R. solani is applied to the surface of the soil. After incubation for 6 days at 27° C. (by day) and 23° C. (by night) and 100% relative humidity (humidity box) in a climatic chamber, fungus attack on the leaf sheath, leaves and stem is evaluated.

(b) Protective local leaf application 12-day-old rice plants are sprayed with a spray mixture prepared from a formulation of the test compound. One day later the treated plants are infected with a suspension of mycelium and sclerotia of R. solani. After incubation for 6 days at 27° C. (by day) and 23° C. (by night) and 100% relative humidity (humidity box) in a climatic chamber, fungus attack on the leaf sheath, leaves and stem is evaluated.

Compounds of the Tables exhibit good activity by inhibiting Rhizoctonia attack. On the other hand, attack was 100% on untreated and infected control plants. Thus e.g. compounds 1.1; 1.15; 1.16; 1.17; 1.28; 1.33; 2.1; 2.3; 2.4; 2.14; 3.1 and 3.3; inhibit fungus attack to 0 to 5%.

What is claimed is:

1. A compound of formula I

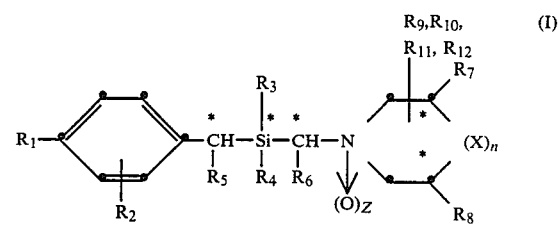

wherein
$R_1$ is hydrogen, $C_1$–$C_{10}$alkyl, $C_3$–$C_7$cycloalkyl, phenyl or trimethylsilyl, $R_2$ is hydrogen or $C_1$–$C_4$alkyl, or $R_1$ and $R_2$ together form a saturated or unsaturated ring containing 6 carbon atoms;

$R_3$ and $R_4$ are each independently of the other hydrogen, $C_1$–$C_4$alkyl or $C_1$–$C_4$alkoxy, and $R_4$ may also be $C_3$–$C_7$cycloalkyl;

$R_5$ to $R_{12}$ are each independently hydrogen or $C_1$–$C_4$alkyl, and $R_8$ and $R_9$ together may also form a saturated or unsaturated ring containing 6 carbon atoms;

X is $CH_2$, oxygen or sulfur, and n and Z are each independently of the other 0 or 1, or, if Z is 0, an acid addition salt thereof.

2. A compound of formula I′

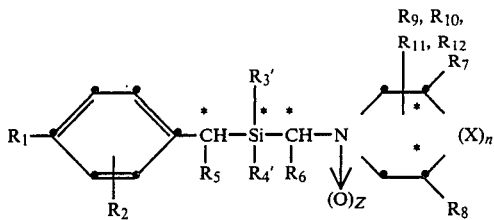

wherein
R$_1$ is hydrogen, C$_1$–C$_{10}$alkyl, C$_3$–C$_7$cycloalkyl, phenyl or trimethylsilyl,
R$_2$ hydrogen or C$_1$–C$_4$alkyl, or
R$_1$ and R$_2$ together form a saturated or unsaturated ring containing 6 carbon atoms;
R$_3'$, R$_4'$ and R$_5$ to R$_{12}$ are each independently hydrogen or C$_1$–C$_4$alkyl, and
R$_8$ and R$_9$ together may also form a saturated or unsaturated ring containing 6 carbon atoms;
X is oxygen or sulfur, and
n and Z are each independently of the other 0 or 1, or, if Z is 0, an acid addition salt thereof.

3. A compound of formula I according to claim 1, wherein
R$_1$ is C$_1$–C$_4$alkyl or trimethylsilyl,
R$_2$ is hydrogen, methyl or ethyl, or
R$_1$ and R$_2$ together form a phenyl ring which is fused in the 3,4-position,
R$_3$ and R$_4$ are each independently of the other methyl, ethyl, methoxy or cyclohexyl,
R$_5$, R$_6$, R$_7$ and R$_8$ are each independently hydrogen, methyl or ethyl,
R$_9$ to R$_{12}$ are each hydrogen, or
R$_8$ and R$_9$ together form a hexane or phenyl ring which is fused in the 3,4-position,
X is oxygen or sulfur,
n is 0 or 1, and
Z is 0.

4. A compound of formula I' according to claim 2, wherein
R$_1$ is C$_1$–C$_4$alkyl or trimethylsilyl,
R$_2$ is hydrogen, methyl or ethyl, or
R$_1$ and R$_2$ together form a phenyl ring which is fused in the 3,4-position,
R$_3'$ and R$_4'$ are each independently of the other methyl or ethyl,
R$_5$, R$_6$, R$_7$ and R$_8$ are each independently hydrogen, methyl or ethyl,
R$_9$ to R$_{12}$ are hydrogen, or
R$_8$ and R$_9$ together form a hexane or phenyl ring which is fused in the 3,4-position,
X is oxygen or sulfur,
n is 0 or 1, and
Z is 0.

5. A compound of formula I' according to claim 4, wherein
R$_1$ is isopropyl, tert-butyl or trimethylsilyl,
R$_2$ is hydrogen, or
R$_1$ and R$_2$ together form a phenyl ring which is fused in the 3,4-position,
R$_3'$ and R$_4'$ are methyl,
R$_5$, R$_6$ and R$_9$ to R$_{12}$ are each hydrogen,
R$_7$ and R$_8$ are each independently of the other hydrogen or methyl,
R$_8$ and R$_9$ together form a hexane or phenyl ring which is fused in the 3,4-position,
X is oxygen or sulfur,
n is 0 or 1, and
Z is 0.

6. A compound of formula I' according to claim 5, wherein
R$_1$ is isopropyl, tert-butyl or trimethylsilyl,
R$_2$ is hydrogen, or
R$_1$ and R$_2$ together form a phenyl ring which is fused in the 3,4-position,
R$_3'$ and R$_4'$ are each methyl,
R$_5$, R$_6$ and R$_9$ to R$_{12}$ are each hydrogen,
R$_7$ and R$_8$ are each independently of the hydrogen or methyl, or
R$_8$ and R$_9$ together form a hexane or phenyl ring which is fused in the 3,4-position,
X is oxygen or sulfur,
n is 1, and
Z is 0.

7. A compound according to claim 2, selected from the group consisting of:
dimethyl-4-tert-butylbenzyl-2,6-dimethylmorpholin-(4)-ylmethyl-silane;
dimethyl-4-tert-butylbenzylmorpholin-(4)-ylmethylsilane;
dimethyl-4-trimethylsilylbenzylmorpholin-(4)-ylmethylsilane;
dimethyl-4-trimethylsilylbenzyl-2,6-dimethylmorpholin-(4)-ylmethylsilane;
dimethyl-4-tert-butylbenzyltetrahydro-1,4-thiazin-(4)-ylmethylsilane;
dimethyl-4-isopropylbenzyltetrahydro-1,4-thiazin-(4)-ylmethylsilane;
dimethyl-4-trimethylsilylbenzyltetrahydro-1,4-thiazin-(4-ylmethylsilane;
and
dimethylnaphthyl-(2)-ylmethyl-2,6-dimethylmorpholin-(4)-ylmethylsilane.

8. A compound of formula I' according to claim 2, which compound is cis-dimethyl-4-tert-butylbenzyl-2,6-dimethylmorpholin-4-ylmethylsilane.

9. A compound of formula I according to claim 1, selected from
cis-cyclohexyl-4-tert-butylbenzyl-2,6-dimethylmorpholin-4-ylmethylsilane and
cis-methoxycyclohexyl-(4-tert-butylbenzyl)-2,6-dimethylmorpholin-(4)-ylsilane.

10. A compound of formula I'

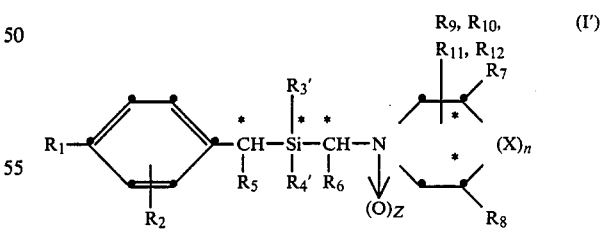

wherein
R$_1$ is hydrogen, C$_1$–C$_{10}$alkyl, C$_3$–C$_7$cycloalkyl, phenyl or trimethylsilyl,
R$_2$ hydrogen or C$_1$–C$_4$alkyl, or
R$_1$ and R$_2$ together form a saturated or unsaturated ring containing 6 carbon atoms;
R$_3'$, R$_4'$ and R$_5$ to R$_{12}$ are each independently hydrogen or C$_1$–C$_4$alkyl, and
R$_8$ and R$_9$ together may also form a saturated or unsaturated ring containing 6 carbon atoms;

X is $CH_2$, and n and Z are each independently of the other 0 or 1, or, if Z is 0, an acid addition salt thereof.

11. A compound of formula I according to claim 1, wherein $R_1$ is $C_1$–$C_4$alkyl or trimethylsilyl, $R_2$ is hydrogen, methyl or ethyl, or $R_1$ and $R_2$ together form a phenyl ring which is fused in the 3,4-position, $R_3$ and $R_4$ are each independently of the other methyl, ethyl, methoxy or cyclohexyl, $R_5$, $R_6$, $R_7$ and $R_8$ are each independently hydrogen, methyl or ethyl, $R_9$ to $R_{12}$ are each hydrogen, or $R_8$ and $R_9$ together form a hexane or phenyl ring which is fused in the 3,4-position, X is $CH_2$, n is 0 or 1, and Z is 0.

12. A compound of formula I' according to claim 11, wherein $R_1$ is $C_1$–$C_4$alkyl or trimethylsilyl, $R_2$ is hydrogen, methyl or ethyl, or $R_1$ and $R_2$ together form a phenyl ring which is fused in the 3,4-position, $R_3'$ and $R_4'$ are independently of the other methyl or ethyl, $R_5$, $R_6$, $R_7$ and $R_8$ are independently hydrogen, methyl or ethyl, $R_9$ to $R_{12}$ are each hydrogen, or $R_8$ and $R_9$ together form a hexane or phenyl ring which is fused in the 3,4-position, X is $CH_2$, n is 0 or 1, and Z is 0.

13. A compound of formula I' according to claim 11, wherein $R_1$ is isopropyl, tert-butyl or trimethylsilyl, $R_2$ is hydrogen, or $R_1$ and $R_2$ together form a phenyl ring which is fused in the 3,4-position, $R_3'$ and $R_4'$ are each methyl, $R_5$, $R_6$ and $R_9$ to $R_{12}$ are each hydrogen, $R_7$ and $R_8$ are each independently of the other hydrogen or methyl, or $R_8$ and $R_9$ together form a hexane or phenyl ring which is fused in the 3,4-position, X is $CH_2$, n is 0 or 1, and Z is 0.

14. A compound of formula I' according to claim 11, wherein $R_1$ is isopropyl, tert-butyl or trimethylsilyl, $R_2$ is hydrogen, or $R_1$ and $R_2$ together form a phenyl ring which is fused in the 3,4-position, $R_3'$ and $R_4'$ are each methyl, $R_5$, $R_6$ and $R_9$ to $R_{12}$ are each hydrogen, $R_7$ and $R_8$ are each independently of the other hydrogen or methyl, or $R_8$ and $R_9$ together form a hexane or phenyl ring which is fused in the 3,4-position, X is $CH_2$, n is 1, and Z is 0.

15. A compound according to claim 10 selected from the group consisting of:

dimethyl-4-tert-butylbenzyl-N-piperidinylmethylsilane;

dimethyl-4-trimethylsilylbenzyl-N-piperidinylmethylsilane;

dimethyl-4-tert-butylbenzyl-N-pyrrolidinylmethylsilane;

dimethyl-4-tert-butylbenzylcyclohexa[c]piperidin-(1)-ylmethylsilane;

dimethyl-4-tert-butylbenzo[c]piperidin-(1)-ylmethylsilane;

dimethyl-4-trimethylsilylbenzylcyclohexa[c]piperidin-(1)-ylmethylsilane; and dimethylnaphthyl-(2)-ylmethylcyclohexa[c]piperidin-(1)-ylmethylsilane.

16. A microbicidal composition for controlling microorganisms or for preventing attack by said microorganisms, which composition contains, as active ingredient, a microbicidally effective amount of at least one compound of formula I according to claim 1 and an adjuvant.

17. A microbicidal composition for controlling microorganims or for preventing attack by said microorganism, which composition contains as active ingredient, a microbicidally effective amount of at least one compound of formula I' as indicated in claim 2 and an adjuvant.

18. A microbicidal composition for controlling microorganims or for preventing attack by said microorganism, which composition contains as active ingredient, a microbicidally effective amount of at least one compound of formula I' as indicated in claim 7 and an adjuvant.

19. A microbicidal composition for controlling microorganims or for preventing attack by said microorganism, which composition contains as active ingredient, a microbicidally effective amount of at least one compound of formula I' as indicated in claim 8 and an adjuvant.

20. A microbicidal composition for controlling microorganims or for preventing attack by said microorganism, which composition contains as active ingredient, a microbicidally effect amount of at least one compound of formula I as indicated in claim 9 and an adjuvant.

21. A composition according to claim 16, which composition contains 0.1 to 99% by weight of a compound of formula I, 99.9 to 1% by weight of a solid or liquid adjuvant, and 0 to 25% by weight of a surfactant.

22. A composition according to claim 21, which composition contains 0.1 to 95% by weight of a compound of formula I or I', 99.8 to 5% by weight of a solid or liquid adjuvant, and 0.1 to 25% by weight of a surfactant.

23. A method of controlling phytopathogenic microorganisms or of protecting cultivated plants from attack by said phytopathogenic microorganisms, which method comprises applying to the plant or to the locus thereof a microbicidally effective amount of a compound of formula I according to claim 1.

24. A method of controlling phytopathogenic microorganisms or of protecting cultivated plants from attack by said phytopathogenic microorganisms, which method comprises applying to the plant or to the locus thereof a microbicidally effective amount of a compound of formula I' according to claim 2.

* * * * *